United States Patent [19]

Terry

[11] Patent Number: 4,917,693
[45] Date of Patent: Apr. 17, 1990

[54] COMPACT DISPOSABLE DIAPER

[76] Inventor: Barbara S. Terry, P.O. Box 40, Red Oak, Ga. 30272

[21] Appl. No.: 275,264

[22] Filed: Nov. 23, 1988

[51] Int. Cl.⁴ .............................................. A61F 13/16
[52] U.S. Cl. ................................................. 604/385.1
[58] Field of Search .................. 604/385.1, 385.2, 386, 604/358, 396, 394

[56] References Cited
U.S. PATENT DOCUMENTS
4,743,240  5/1988  Powell .............................. 604/385.1

Primary Examiner—John D. Yasko
Attorney, Agent, or Firm—Hurt, Richardson, Garner, Todd & Cadenhead

[57] ABSTRACT

A compact disposable diaper is disclosed having flap-like compartments on opposed ends of the rear portion of the diaper assembly for retaining cleansing and drying towelettes for use in clean up of a child when changing the diaper. The compartments are sealed by conventional closure means and are kept free from access by the child by fastening the standard adhesive tabs on the front portion over the exterior surface of the flap-like compartments on the rear portion.

8 Claims, 1 Drawing Sheet

COMPACT DISPOSABLE DIAPER

REFERENCE TO RELATED APPLICATION

This is a continuation-in-part of application Ser. No. 07/107,957, filed Oct. 13, 1987, now abandoned.

BACKGROUND OF THE INVENTION

This invention relates to a new configuration for a compact disposable diaper structure in which the flaps used to form a closure around the child have openings in which wet and dry towelettes can be inserted for use in cleaning the child.

The prior art contains numerous patents which address the problem of absorption of the child's wetness. This is accomplished generally by including one or more additional layers between the backing layer of the diaper, which is in contact with the infant and the outer or top sheet. A few prior art patents deal with the remaining major problem with disposable diapers which is the problem of solid waste remaining on the child when the diaper is removed necessitating cleanup. The problem is aggravated when traveling away from home with the child when it becomes necessary to change a soiled diaper.

The patent to Ehrlich, U.S. Pat. No. 4,221,221, discloses a utility diaper structure having a plurality of container assemblies connected to the diaper structure. The diaper structure is of conventional type, size and shape with a standard connector assembly to aid in connection of the upper edges of the diaper. The container assemblies are a plurality of sealed members each of which are connected to the main body member. The container assemblies comprise: a powder packet assembly having a baby powder material sealed within a container member; a towel packet assembly having a towel member sealed within a container member; and a baby oil packet assembly having a baby oil material sealed within a container member. The baby care elements are used and then disposed of while the remaining diaper assembly is utilized in a conventional manner.

The patent to Norris, U.S. Pat. No. 4,417,894, discloses an improved diaper containing a towelsheet superimposed on or above the back of a diaper. When the diaper is messy the towel sheet is unfastened at the bottom area of the diaper, removed and then used as a towel to clean solid waste from a child as part of the diaper change process. The towel sheet is sandwiched between the absorbent body and the back sheet and is fastened to the diaper at the top lateral edge only. It is thus free on the bottom lateral edge and the side lateral edges. A multiplicity of towel sheets can be used to clean more effectively.

The patent of Critsofolo, U.S. Pat. No. 4,428,477, discloses a resealable package for premoistened towelettes comprising a sheet of flexible moisture-impermeable material folded about the towelettes and then heat sealed to form an inverted T-shape container enclosing the towelettes within the base of the "T". One of the flaps of the sheet material in the stem of the "T" is provided with a region of weakening that is spaced from the base of the "T" for opening and dispensing the towelettes.

SUMMARY OF THE INVENTION

It is therefore an object of this invention to provide a compact disposable diaper structure having built-in compartments for holding wet and dry towelettes or other baby maintenance items.

It is a further object of this invention to provide an integral compact disposable diaper structure containing baby clean up items in sealed pockets which can be retained in the diaper while it is being worn by the child.

It is a still further object of this invention to provide a compact disposable diaper structure in which baby clean up items can be kept in internal pockets which are inaccessible to the child while the diaper is being worn.

Still other objects, features and attendant advantages of the present invention will become apparent to those skilled in the art from a reading of the following detailed description of the preferred embodiment, taken in conjunction with the accompanying drawings.

These and other objects are achieved by a compact disposable diaper structure in which the final structure after stitching resembles a T-shape. This particular shape allows the rear upper edge portion to have a greater width than the remainder of the diaper structure to form flap-like extensions wherein the compartments for retaining the baby car items are formed.

DETAILED DESCRIPTION OF A PREFERRED EMBODIMENT

Figure 1:
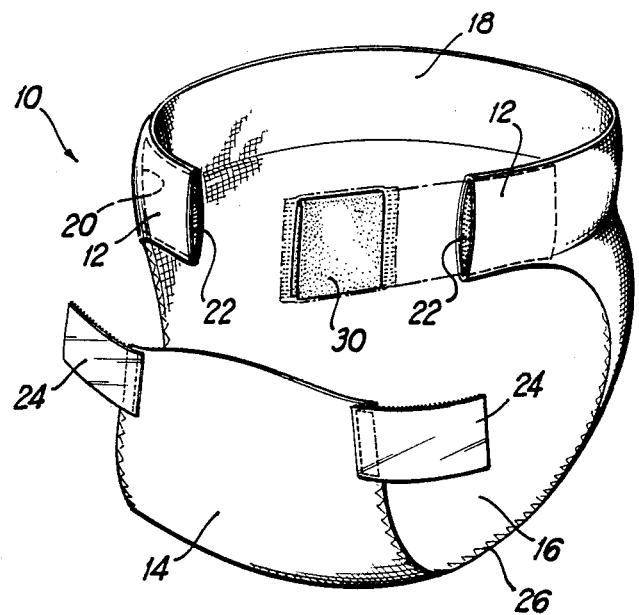
FIG. 1 is a perspective view of the compact disposable diaper structure illustrating the location of the sealed compartments.

Referring to FIG. 1, there is shown a perspective view of the compact disposable diaper 10 as it is intended to be positioned on the child before fastening. The compact disposable diaper 10 includes a diaper assembly having a front portion 14, a seat portion 16, and an rear portion 18. The rear portion 18 termintes on both edges with a flap-like extension 12 containing compartment or pocket 20. Tabs 22 or similar closure means, such as that sold under the trademark Velcro ®, are disposed on the open end of pocket 20 for sealing a cleansing or drying towelette inside. Conventional pressure sensitive adhesive tabs 24 are provided on the edges of front portion 14 as fastening means to provide a conventional disposable diaper connector assembly that will retain the diaper in place on the child's body. The side walls 26 of the diaper are elasticized, by sewing in resilient means such as an elastic band, to provide a contoured assembly that will provide a more secure fit to the child.

Figure 2:
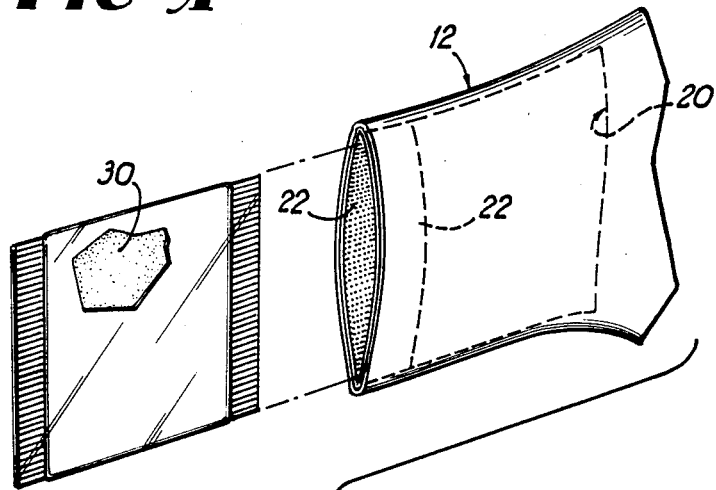
FIG. 2 is an enlarged view of one sealed compartment also showing the packaging of a typical towelette.

FIG. 2 is an enlarged perspective view of the flap-like extension 12 of the diaper assembly shown in FIG. 1. It shows the compartment 20 for retaining the cleansing and drying towelettes 30 or other baby cleanup items. The towels 30 are folded and inserted inside compartments 20. The cleansing towelette is pre-packaged within an aluminum foil enclosure before placement in compartment 20. The compartments 20 are secured by Velcro ® tabs 22 on the open end.

The main body of diaper assembly 10 is of a generally rectangular shape initially. The T-shape results when the seat portion 16 of diaper 10 is elasticized by sewing in an elastic band. This serves to draw in the material within seat portion 16 and makes the unelasticized rear portion 18 takes on a flap-like appearance. Unlike other prior art diapers, compartments 20 form an integral part of compact disposable diaper 10 for retaining baby cleansing items in a manner such that the contents of the compartments are completely impervious to soiling of the diaper, the compartments are safe and child-proof in the sense that the compartments are not accessible to the child while the diaper is being worn, and the contents of the compartments are easily accessible to a parent or other attendant during clean up operation.

In summary, the present invention provides a convenient, economical device which will facilitate clean up of a child in public places upon removal of a soiled diaper by the escorting parent or attendant. The device differs from prior art devices in that the compartments containing the baby clean up items are an integral part of the diaper structure and the cleansing and drying towelette packages are retained in the compartments while the diaper is being worn by the child. Thus, the parent or attendant taking a child out in public does not have to be concerned about carrying another diaper containing pre-packaged cleansing items, or in the alternative, carrying baby maintenance items separately.

While an embodiment of a compact disposable diaper has been shown and described in detail herein, various additional changes and modifications may be made without departing from the scope of the present invention. The term child in the following claims is intended to encompass children from newborn infants through toddlers who still require the use of diapers.

What is claimed is:

1. A compact disposable diaper adapted for use with a child, comprising:
    a diaper assembly having a front portion, a seat portion, and a rear portion connected together and with each of said portions having opposed side walls and opposed edges, said diaper assembly being adapted to be worn around the crotch region of the child;
    there being provided a pair of open-ended compartments in the opposed edges of said rear portion and respectively adjacent to the top corners of said diaper assembly;
    a baby maintenance item disposed within each of said compartments;
    closure means on the edges of the side walls at the top of said rear portion for closing said compartments, for removeably retaining said baby maintenance items within said compartments; and
    fastening means on the opposed side walls of said front portion for attaching said front portion to said rear portion so that a part of said front portion overlies said compartments and for retaining the diaper assembly in place on the child.

2. A compact disposable diaper as claimed in claim 1 wherein said resilient means comprises an elastic band sewn into the side walls of said seat portion.

3. A compact disposable diaper as claimed in claim 1 wherein said baby maintenance item is a cleansing towelette.

4. A compact disposable diaper as claimed in claim 1 wherein said baby maintenance item is a drying towelette.

5. A compact disposable diaper adapted for use with a child comprising a diaper assembly including:
    a rear portion having opposed ends at the top with open-ended compartments respectively in each of said opposed ends;
    a baby maintenance item disposed within each of said compartments;
    closure means on the edges of said compartments for respectively closing said compartments for retaining said baby maintenance items within said compartments;
    a seat portion connected to said rear portion and having opposed side walls;
    resilient means disposed within the opposed side walls of said seat portion for urging the side walls to provide a secure fit around the child; and
    a front portion connected to said seat portion and including adhesive tabs for fastening said front portion to said rear portion and over said opposed ends of said rear portion to overlie said compartments.

6. A compact disposable diaper as claimed in claim 5 wherein said resilient means comprises an elastic band sewn into the sidewalls of said seat portion.

7. A compact disposable diaper as claimed in claim 5 wherein said baby maintenance item is a cleansing towelette.

8. A compact disposable diaper as claimed in claim 5 wherein said baby maintenance item is a drying towelette.

* * * * *